(12) United States Patent
Green et al.

(10) Patent No.: US 7,413,900 B2
(45) Date of Patent: Aug. 19, 2008

(54) IMMORTALIZED FIBROBLASTS

(75) Inventors: Howard Green, Brookline, MA (US); Shiro Iuchi, Quincy, MA (US); Walid Kuri-Harcuch, Naucalpan (MX); Meytha Marsch-Moreno, Naucalpan (MX)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/263,549

(22) Filed: Oct. 31, 2005

(65) Prior Publication Data

US 2007/0098696 A1 May 3, 2007

(51) Int. Cl.
*C12N 5/06* (2006.01)
*C12N 5/02* (2006.01)

(52) U.S. Cl. .................. 435/357; 435/354; 435/325

(58) Field of Classification Search .............. None
See application file for complete search history.

(56) References Cited

U.S. PATENT DOCUMENTS

| | | | | |
|---|---|---|---|---|
| 5,284,755 A * | 2/1994 | Gearing et al. | ............. | 435/69.1 |
| 5,453,357 A | 9/1995 | Hogan | | |
| 5,843,780 A * | 12/1998 | Thomson | ................... | 435/363 |
| 6,200,806 B1 | 3/2001 | Thomson | | |
| 2002/0072117 A1 | 6/2002 | Xu et al. | | |
| 2003/0017589 A1 | 1/2003 | Mandalam et al. | | |
| 2005/0148070 A1 | 7/2005 | Thomson et al. | | |
| 2005/0153445 A1 | 7/2005 | Mandalam et al. | | |

OTHER PUBLICATIONS

Todaro et al. Quantitative studies of the growth of mouse embryo cells in culture and their development into established lines. J. Cell Biol. 17:299-313,1963.*
Park et al. Establishment and maintenance of human embryonic stem cells on STO, a permanently growing cell line. Biol. Reprod. 69:2007-2014, 2003.*
Boiani et al., Oct4 distribution and level in mouse clones: consequences for pluripotency. Genes Dev. May 15, 2002;16(10):1209-19.
Green et al., Growth of cultured human epidermal cells into multiple epithelia suitable for grafting. Proc Natl Acad Sci USA. Nov. 1979;76(11):5665-8.
Green, H. et al., Marker succession during the development of keratinocytes from cultured human embryonic stem cells. Proc Natl Acad Sci USA Dec. 23, 2003;100(26):15625-30. Epub Dec. 8, 2003.
Iuchi et al., Oligomeric and polymeric aggregates formed by proteins containing expanded polyglutamine. Proc Natl Acad Sci USA. Mar. 4, 2003;100(5):2409-14. Epub Feb. 18, 2003.
Matin et al., Specific knockdown of Oct4 and beta2-microgloblin expression by RNA interference in human embryonic stem cells and embryonic carcinoma cells. Stem Cells. 2004;22(5):659-68.
Nichols et al., Formation of pluripotent stem cells in the mammalian embryo depends on the POU transcription factor Oct4. Cell. Oct. 30, 1998;95(3):379-91.

Niwa et al., Quantitative expression of Oct-3/4 defines differentiation, dedifferentiation or self-renewal of ES cells. Nat Genet. Apr. 2000;24(4):372-6.
Pesce et al., Oct-4: gatekeeper in the beginnings of mammalian development. Stem Cells. 2001;19(4):271-8. Review.
Rheinwald et al., H. Serial cultivation of strains of human epidermal keratinocytes: the formation of keratinizing colonies from single cells. Cell. Nov. 1975;6(3):331-43.
Robertson et al., Embryo-derived stem cell lines. From: Teratocarcinomas and Embryonic Stem Cells: A Pratical Approach. E. J. Robertson, Oxford, UK. IRL Press. 1987:71-112.
Scholer. et al., A family of octamer-specific proteins present during mouse embryogenesis: evidence for germline-specific expression of an Oct factor. EMBO J. Sep. 1989;8(9):2543-50.
Scholer et al., Oct-4: a germline-specific transcription factor mapping to the mouse t-complex. EMBO J. Jul. 1990;9(7):2185-95.
Scholer et al., Octamer binding proteins confer transcriptional activity in early mouse embryogenesis. EMBO J. Sep. 1989;8(9):2551-7.
Scholer, Octamania: the POU factors in murine development. Trends Genet. Oct. 1991;7(10):323-9.
Schuldiner et al., Effects of eight growth factors on the differentiation of cells derived from human embryonic stem cells. Proc Natl Acad Sci USA. Oct. 10, 2000;97(21):11307-12.
Shamblott et al., Human embryonic germ cell derivatives express a broad range of developmentally distinct markers and proliferate extensively in vitro. Proc Natl Acad Sci U S A. Jan. 2, 2001;98(1):113-8.
Thomson et al., Embryonic stem cell lines derived from human blastocysts. Science. Nov. 6, 1998;282(5391):1145-7. Erratum in: Science Dec. 4, 1998;282(5395):1827.
Thomson et al., Human embryonic stem cell and embryonic germ cell lines. Trends Biotechnol. Feb. 2000;18(2):53-7.
Thomson et al., Isolation of a primate embryonic stem cell line. Proc Natl Acad Sci USA. Aug. 15, 1995;92(17):7844-8.
Velkey et al., Oct4 RNA interference induces trophectoderm differentiation in mouse embryonic stem cells. Genesis. Sep. 2003;37(1):18-24.
Ware et al., Inherited resistance to N- and B-tropic murine leukemia viruses in vitro: evidence Virology. Nov. 1972;50(2):339-48.
Zhang et al., Embryonic mouse STO cell-derived xenografts express hepatocytic functions in the livers of nonimmunosuppressed adult rats. Stem Cells. Feb. 2005;23(2):186-99.

* cited by examiner

*Primary Examiner*—Quang Nguyen
(74) *Attorney, Agent, or Firm*—Wolf Greenfield & Sacks

(57) ABSTRACT

Aspects of the invention provide an immortalized fibroblast cell line capable of the growth and maintenance of human embryonic stem cells. An immortalized fibroblast cell line derived from an early stage mouse embryo is provided. Methods of preparing an immortalized fibroblast cell line from an early stage mouse embryo are also provided.

1 Claim, 6 Drawing Sheets

MMM

MMMbz

IMMORTALIZED FIBROBLASTS

GOVERNMENT SUPPORT

This invention was made in part with government support under Grant No. R01 GM068478-02 from the National Institutes of Health (NIH). The government may have certain rights in the invention.

FIELD OF THE INVENTION

Aspects of the invention relate to an immortalized fibroblast cell line established from an embryo and methods of preparing an immortalized fibroblast cell line.

BACKGROUND OF THE INVENTION

Fibroblast cell lines have been used as supporting cells for the growth of other cells for decades. The fibroblast cell lines generally used for this purpose are 3T3 cells and MEF cells. The 3T3 cell line was first described in 1963 (Todaro, G. J. and Green, H., 1963, *J. Cell Biol.*, 17:299-313). The 3T3 cell line is an immortalized fibroblast cell line derived from mouse embryos 17 to 19 days old. The 3T3 cell line, however, is not suitable for growing and maintaining pluripotency of embryonic stem cells.

More recently, a source of supporting cells was described, freshly derived mouse embryonic fibroblasts (MEFs) (Robertson, E. J., 1987, Embryo-derived stem cell lines, *Teratocarcinomas and Embryonic Stem Cells: A Practical Approach*, E. J. Robertson, Oxford, UK, IRL Press). The MEF cell line is derived from mouse embryos 13-14 days old and is not an immortalized cell line. The MEF cell line, unlike 3T3 cells, can be used for growing and maintaining the pluripotency of embryonic stem cells. MEF supporting cells have become the standard for growing and maintaining embryonic stem cells in serum free media. These fibroblasts, however, have drawbacks including a short lifetime in culture and the need for repeated isolation.

A need exists for an immortalized fibroblast cell line that has at least the embryonic supporting properties of MEF cells.

SUMMARY OF THE INVENTION

According to one aspect of the invention, a composition is provided. The composition includes an immortalized fibroblast cell line established from a mouse embryo less than 15 days old and immortalized by serial passages. In some embodiments, the mouse embryo is between 12 and 13 days old. In certain embodiments, the immortalized fibroblast cell line, in a confluent layer, supports the growth and maintenance of Oct4 positive H9 human embryonic stem cells, preferably substantially free of dome-shaped H9 cells. In some embodiments, the cell line contains a recombinant drug resistance gene. In certain embodiments, at least the majority of the H9 human embryonic stem cells are angular-shaped when cultured on the immortalized fibroblasts of the invention. In some embodiments, the cell line is MMM cells, or progeny thereof, deposited with the ATCC under accession number PTA-7190.

According to another aspect of the invention, a composition is provided. The composition includes an immortalized fibroblast cell line that, when in a confluent layer, supports the growth and maintenance of Oct4 positive H9 human embryonic stem cells substantially free of H9 dome-shaped cells. In some embodiments, the immortalized fibroblast cell line contains a recombinant drug resistance gene. In certain embodiments, at least the majority of the H9 human embryonic stem cells are angular-shaped when cultured on the immortalized fibroblasts.

According to another aspect of the invention, methods are provided for preparing an immortalized fibroblast cell line. Cells are provided from a mouse embryo less than 15 days old and passaged serially to produce an immortalized fibroblast cell line. In some embodiments, the mouse embryo is between 12 and 13 days old. In certain embodiments, the cells from the mouse embryo are passaged at least 20 times, 25 times, 30 times, 40 times, 50 times, 60 times, or 65 times. In some embodiments, the methods further include introducing a recombinant drug resistance gene into the immortalized cell line. In certain embodiments, the methods further include determining that the immortalized fibroblast cell line supports the growth and maintenance of Oct4 positive H9 human embryonic stem cells, preferably substantially free of H9 dome-shaped cells, by seeding the H9 human embryonic stem cells on a confluent layer of the immortalized fibroblast cells in serum free medium.

These and other aspects of the invention are described below.

DETAILED DESCRIPTION OF THE INVENTION

Figure 1A:
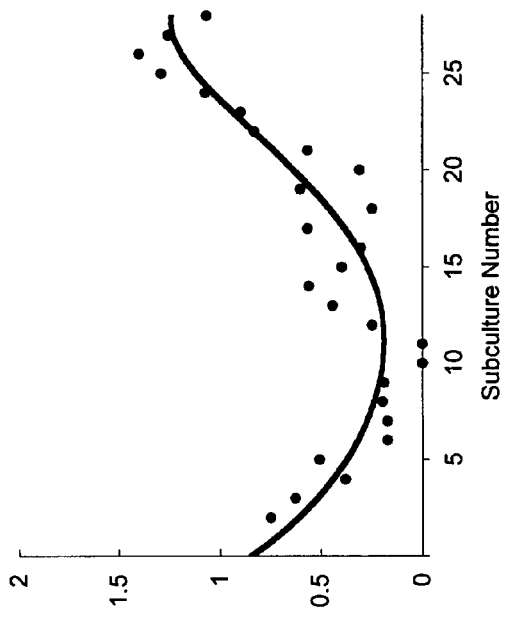
FIG. 1. A) Graph showing growth rate of day 12-13 embryonic mouse fibroblasts upon serial transfer during establishment of the MMM line. B) Graph showing the number of population doublings during each subculture calculated by the formula: $n=3.32(\log_{10}N_f - \log_{10}N_i)$, where n is the number of population doublings, $N_f$ is the number of cells harvested and $N_i$ the number of cells inoculated.

The invention relates to methods of preparing an immortalized fibroblast cell line. It was discovered according to various aspects of the invention that immortalized fibroblast cells can be derived from mouse embryos harvested earlier than day 17. These cells are capable of maintaining the growth of human embryonic stem cells. They also can support pluripotency as well as or better than MEF cells. Methods of preparing such immortalized cell lines are provided.

The term "immortalized", when used in connection with the fibroblast cell lines of the invention, means those capable of unlimited passage when maintained under suitable growth conditions. The cells of the invention are "immortalized" by serial passages.

In aspects of the invention, an immortalized fibroblast cell line is established from a mouse embryo that is 15 days old or less. In some embodiments, the cell line is established from a mouse embryo that is less than 15 days old, for example 13, 12, 11, or less days old. It is necessary only that sufficient fibroblastic cells (fusiform in appearance) be available for harvest and growth. In certain embodiments, the embryo is between 12 and 13 days old.

One of ordinary skill in the art will appreciate that a 12-13 day window may include a window of 6, 12, or even 18 hours off of the 'actual' embryo age, using conventional techniques for determining embryo age. For example, one such technique involves observing the formation of a hard mucous plug in the vaginal area of a mouse, after having left mice overnight for mating. The day of detection of this plug is denoted as day zero and the development of the embryo is timed from this date. In some techniques, the formation of the plug is observed at midday, after having left mice overnight for mating, and the age is recorded as day one-half.

In the examples below, the age of an embryo is determined according to the Thieler gestational stage. Mouse embryos can be staged according to a variety of criteria, as described by Theiler in "The House Mouse: Atlas of Mouse Development" (Springer-Verlag, New York, 1989). To distinguish the phases of early development these stages may be supplemented by, for example, cell number, somite number or those characteristics described by Downs and Davies (1993), *Development*, 118:1255. Embryos of the same gestational age may differ in their stage of development.

In aspects of the invention, cells are isolated from an embryo using standard techniques known to those of ordinary skill in the art. One non-limiting example of an isolation procedure is as follows. Briefly, one or more embryos are removed from a mouse under aseptic conditions and the head and viscera removed and discarded. The embryos are rinsed and minced in PBS containing trypsin and incubated at 37° C. in trypsin containing EDTA for 10 minutes. The tissue fragments are allowed to settle and nutrient media is added to the cell suspension. The cells are cultured in media at 37° C., 10% $CO_2$, avoiding confluence. Once the cells are at about 75% of confluence, the cells are serially cultured. A further example is described in Example 2.

Aspects of the invention include methods for preparing an immortalized fibroblast cell line by the culture of fibroblast cells derived from a mouse embryo. In some embodiments, embryonic fibroblast cells may be placed on a surface adapted for cell attachment. As used herein, the term "adapted for cell attachment" includes surfaces on which embryonic fibroblast cells will adhere. Examples of surfaces that are adapted for cell attachment include, but are not limited to, standard tissue culture plates, tubes, flasks and microtitre well plates of various sizes (for example 12 wells per plate, 24 wells per plate, 48 wells per plate or 96 wells per plate), which may have hydrophilic surfaces to enhance adhesion of cells for growth in culture. It will be understood that the shape or form of a surface that is adapted for cell attachment can vary and may include shapes such as tubes, straws, wells etc. In one embodiment, the cells are grown in a nutrient medium under suitable growth conditions. "Suitable growth conditions" as used herein is an environment in which cells of interest will proliferate in vitro. The environment is meant to include nutrient medium in which the cells are cultured, a supporting structure (such as a substrate solid surface), and appropriate incubation conditions such as temperature, oxygen, etc.

A "nutrient medium" as used herein is a medium for culturing cells containing nutrients that promote proliferation. The nutrient medium may contain any of the following in an appropriate combination: isotonic saline, buffer, amino acids, serum or serum replacement, and other exogenously added factors. In some embodiments, the nutrient medium may contain one or more drugs used for selection of a cell having a particular characteristic. In some embodiments the nutrient medium is serum free. Nutrient medium is commercially available from sources such as Life Technologies (Gaithersburg, Md.).

An immortalized fibroblast cell line is prepared by performing serial consecutive transfers known in the art as "passaging". A passage, as understood by those of ordinary skill in the art, involves the removal of cells from, for example, a tissue culture flask and sub-culturing a fraction of those cells into a fresh tissue culture flask, or other container suitable for growing cells, containing fresh nutrient medium. Trypsin is commonly used to remove the adherent cells from the surface of the tissue culture flask and is available commercially from, for example, GIBCO® (INVITROGEN™, Carlsbad, Calif.). In certain embodiments, the cells are passaged at 15,000 cells per square centimeter of vessel surface. A serial passage occurs when the cells are continuously transferred from a sub-confluent layer of cells into a fresh tissue culture flask, at a lower cell density to allow the cells to grow.

In some embodiments, the cells may be passaged when they are at about 75% of confluence. It is preferred to harvest the cells for passage prior to the cells reaching confluence, because confluence can promote variants within the cell line. A convenient harvesting stage is at about 75% of confluence, i.e., about 75% of the vessel surface upon which the cells are growing is covered with cells. It will be understood that the cells need not be harvested at 75% of confluence, but instead could be harvested at virtually any level of sub-confluence. The cells could even be harvested at confluence, although subject to the attendant risk described above, which, in general, it is desirable to avoid.

In certain embodiments, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, or 100 consecutive passages may be performed to establish an immortalized fibroblast cell line of the invention.

One example of an aspect of the invention is an immortalized fibroblast cell line prepared as shown in Example 1 and designated as MMM cells. An immortalized fibroblast cell line of MMM cells includes progeny cells. This example of an immortalized fibroblast cell line has been deposited with the American Type Culture Collection 10801, University Blvd., Manassas, Va. 20110-2209 U.S.A., under accession number PTA-7190. The immortalized fibroblast cell line designated as "MMM cells" was mailed by Federal Express to the ATCC by Howard Green of Harvard Medical School on Oct. 28, 2005.

In aspects of the invention, the immortalized fibroblast cell lines are capable of supporting the growth and maintenance of a second cell type, to provide an environment in which the cells of the second type can grow. In some embodiments such supporting cells are referred to as feeder cells or feeders. The second cell type can be a stem cell (e.g., an embryonic stem cell, a bone marrow stem cell, a cord blood stem cell, etc.) or it can be a more differentiated cell type (e.g., a keratinocyte).

In some embodiments, the growth and maintenance of human embryonic stem cells on immortalized fibroblast cells is performed by inoculating or seeding a confluent layer of immortalized fibroblast cells with human embryonic stem cells. A confluent layer of immortalized fibroblast cells prevents the supported human embryonic stem cells from adhering to the container in which they are being grown.

An immortalized fibroblast cell line may be irradiated or treated chemically, for example with mitomycin, prior to use as a feeder cell line, to prevent multiplication of the cells without killing the cells. In some embodiments, the immortalized fibroblast cells are irradiated prior to inoculation with H9 human embryonic stem cells. Irradiation of an immortalized fibroblast cell line can be performed using standard techniques known to those of ordinary skill in the art. In certain embodiments, the irradiated immortalized fibroblast cells are inoculated at a concentration that ensures the cells cover the full surface of the container. In some embodiments, the irradiated immortalized fibroblast cells are inoculated at $1.2 \times 10^5/cm^2$ or $1.5 \times 10^5/cm^2$ to provide a confluent layer of cells.

In some embodiments, an embryonic stem (ES) cell is a pluripotent cell derived from pre-implantation embryos. ES cells have the capacity to differentiate into any cell type in vivo, and to differentiate into many different cell types in vitro. In certain embodiments, conditions for supporting an embryonic stem cell line are maintained. In some embodiments, the cells are grown in the absence of antibiotics. In other embodiments, the cells are grown in the presence of antibiotics. In some embodiments, the cells are grown in the absence of serum.

As a non-limiting example, a stem cell line such as prototype primate pluripotent stem cells (pPS cells) may be supported by immortalized fibroblast cells of the invention. pPS cells are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture. Staining techniques and markers are known to those of ordinary skill in the art. pPS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population.

Cultures that are substantially undifferentiated contain at least 20% undifferentiated pPS cells, and may contain at least 40%, 60%, 80%, 90% or 100% (in terms of percentage of cells with the same genotype that are undifferentiated). In certain embodiments, the percentage of undifferentiated pPS cells is at least 90%. Examples of such cells are disclosed in Thomson et al., 1998, *Science*, 282:1145 and U.S. Pat. No. 6,200,806, the entire contents of which are herein incorporated by reference.

pPS cells include, without limitation, embryonic cells of various types, exemplified by human embryonic stem (hES) cells, defined below; embryonic stem cells from other primates, such as Rhesus or marmoset stem cells (Thomson et al., (1995), *Proc. Natl. Acad. Sci. USA*, 92:7844; Thomson et al., 1998, *Developmental Biology*, 38:133); and human embryonic germ (hEG) cells (Shambloft et al., (1998), *Proc. Natl. Acad. Sci. USA*, 95:13726). Any cells of primate origin that are capable of producing progeny that are derivatives of all three germinal layers are included, regardless of whether they were derived from embryonic tissue, fetal tissue, or other sources. It is beneficial to use pPS cells that are karyotypically normal and not derived from a malignant source.

A prototype human embryonic stem cell (hES cell) includes, without limitation, pluripotent stem cells that are derived from a human embryo at the blastocyst stage, or before substantial differentiation of the cells into the three germ layers. Those skilled in the art will appreciate that except where explicitly required otherwise, the term includes primary tissue and established lines that bear phenotypic characteristics of hES cells, and derivatives of such lines that still have the capacity of producing progeny of each of the three germ layers.

A prototype human embryonic stem cell (hES cell) may be a H9 human embryonic stem cell. The H9 human embryonic stem cell line was derived from a human embryo obtained from the Rambam Medical Center in Hafia, Israel by Thomson et al. (Thomson, J. A. and Odorico, J. S., 2000, *Trends Biotechnol.*, 18:53-57). The H9 human embryonic stem cells were prepared from the inner mass of a human blastocyst and cultured to produce a H9 embryonic stem cell line.

Figure 3:
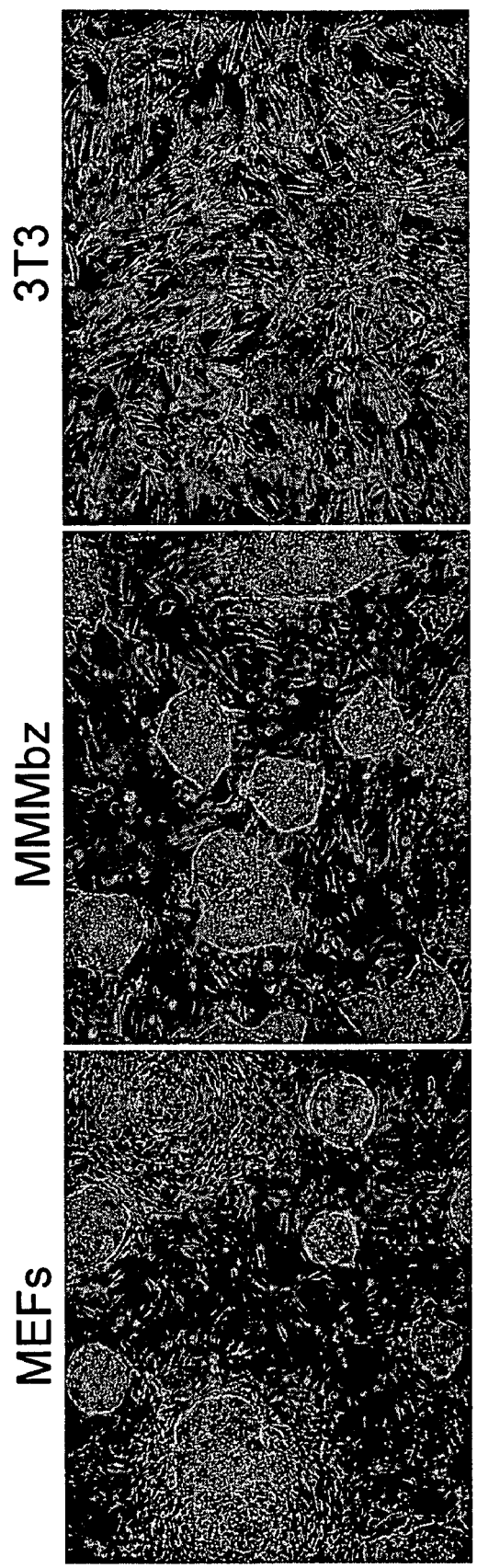
FIG. 3. Phase microscopy showing the appearance of H9 colonies grown on three supporting cell types.

In aspects of the invention, human embryonic stem cells are maintained such that the cells remain Oct4 positive. In some embodiments, the human embryonic stem cells, when grown on a confluent layer of the immortalized fibroblasts of the invention, are substantially free of dome-shaped stem cells. Substantially free refers to there being no more than 25% (and preferable no more than 10%, 5%, 3%, or even 2%) dome-shaped human embryonic stem cell colonies in the population of human cells grown on the confluent layer of the immortalized cells of the invention. A non-limiting example of a dome-shaped human embryonic stem cell is depicted in FIG. 3, showing H9 human embryonic stem cells grown on MEF cells. In certain embodiments, the human embryonic stem cells are maintained such that the majority of the stem cells are angular-shaped. In some embodiments, the majority refers to at least 50%, but more preferably 75%, 90%, 95% or even 98% of the human embryonic stem cells are angular-shaped. A non-limiting example of an angular-shaped human embryonic stem cell is shown in FIG. 3 showing H9 human embryonic cells grown on MMMbz cells.

In certain aspects of the invention, an immortalized cell line of the invention can be identified by testing it to determine whether it is capable of supporting the growth and maintenance of human embryonic stem cells, such as H9 embryonic stem cells. In some embodiments, the growth and maintenance of human embryonic stem cells is determined by measuring expression levels of the marker Oct4. The Oct4 marker is a known marker that can be used to detect embryonic stem cells. The Oct4 marker is a member of the Oct family of transcription factors that are involved in regulation of tissue- and cell-specific transcription and in transcription of housekeeping genes. Oct4 is known as a transcription factor expressed by undifferentiated embryonic stem cells and embryonic germ cells. The expression of Oct4 can be detected using an antibody directed against Oct4. Oct4 antibodies are commercially available, for example from Abcam (Cambridge, Mass.). The expression of Oct4 may be determined using detection methods such as ELISA, Western blotting, immunoprecipitation, and immunohistochemical techniques as known to those of ordinary skill in the art. In some embodiments, cells that have retained Oct4 marker expression are angular shaped. In certain embodiments, cells showing regions of loss of Oct4 marker expression are dome-shaped. In certain embodiments, cells may be mosaic colonies having both angular shaped cells and dome-shaped cells.

In aspects of the invention, immortalized fibroblast cells may contain a recombinant drug resistance gene. In some embodiments, a recombinant drug resistance gene may be incorporated or introduced into a cell, such as an immortalized fibroblast cell. One of ordinary skill in the art would understand that incorporated or introduced refers to the incorporation or insertion of a recombinant gene into a cell, stably or otherwise. A recombinant gene may be incorporated into a cell by transfecting a cell with a vector containing the recombinant gene.

As used herein, a "vector" may be any of a number of nucleic acids into which a desired sequence may be inserted by restriction and ligation for transport between different genetic environments or for expression in a host cell. A vector is preferably composed of DNA, although RNA vectors are alternatives. Vectors include, but are not limited to, plasmids, phagemids, bacteria and virus genomes, such as adenovirus and poxvirus.

A DNA sequence encoding a recombinant drug resistance gene may be inserted into a vector by restriction and ligation such that it is operably joined to regulatory sequences and may be expressed as an RNA transcript. The vector is one which is able to replicate in a host cell or be replicated after its integration into the genome of a host cell, and which is further characterized by one or more endonuclease restriction sites at which the vector may be cut in a determinable fashion and into which a desired DNA sequence may be ligated such that the new recombinant vector retains its ability to replicate in the host cell. A recombinant drug resistance gene may be transfected into an immortalized fibroblast cell such that the immortalized fibroblast cell obtains resistance to the particular drug.

As used herein, a coding sequence and regulatory sequences are said to be "operably" joined when they are covalently linked in such a way as to place the expression or transcription of the coding sequence, such as a coding sequence encoding a recombinant drug resistance gene, under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide. Such a promoter may be a constitutive promoter or an inducible promoter, and may also be such that it (only) provides for expression in a specific stage of development of the host cell or host organism, and/or such that it (only) provides for expression in a specific cell, tissue, organ or part of a multicellular host organism.

Various techniques may be employed for introducing a vector containing a recombinant drug resistance gene into a cell. The term "transfection" as used herein refers to the introduction of foreign DNA into cells. Such techniques include calcium phosphate precipitate transfection, DEAE transfection, transfection or infection with viruses, liposome-mediated transfection (lipofection), ballistic transformation, (micro-)injection, transfection, electroporation and the like. Stable transfection of a cell line is preferred, and this can be tested using selectable markers present in the vector. The presence of a selectable marker allows the selection of those cells which contain the vector. Selectable markers include but are not limited to for example, recombinant antibiotic resistance genes and recombinant mitomycin resistance genes. In some embodiments, the drug resistance gene for antibiotics such as ampicillin, neomycin, kanamycin, blasticidin, zeocin or any analogs of the aforementioned, may be transfected into an immortalized fibroblast cell. In certain embodiments, a recombinant drug gene for both blasticidin and zeocin may be transfected into an immortalized fibroblast cell. A successfully transfected cell can be distinguished from a non-transfected cell by growing the cells in the presence of the drug to which the cells have been conferred resistance. Cells containing the drug resistance gene will survive and cells that are absent the drug resistance gene will not. In certain embodiments, a recombinant drug resistance gene is transfected into an immortalized fibroblast cell line and separately a similar recombinant drug resistance gene is transfected into a human embryonic stem cell to be supported by the immortalized fibroblast cell line.

Where liposomes are employed to deliver the vector containing a recombinant drug resistance gene, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver recombinant drug resistance genes into cells, as is known by those skilled in the art. Liposomes are commercially available from Life Technologies, Inc., for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, 3:235-241 (1985).

EXAMPLES

Example 1

Derivation of MMM Cell Line

Cells were isolated from a mouse embryo 12-13 days old and cultured in D-MEM media (Eagle's medium modified by Dulbecco-Vögt, Life Technologies (Invitrogen), Gaithersburg, Md.) supplemented with 10% calf serum and gentamycin to prepare a primary culture. The cells were incubated at 37° C., 10% $CO_2$ until they reached about 75% of confluence. The cells were washed with sterile phosphate buffered saline (PBS) and trypsin was added to remove the adhered cells from the surface of the flask. The cells were resuspended in media and counted using a hemocytometer. The cells were passaged into fresh media and applied to the surface of the vessel at 15,000 cells per square centimeter and incubated at 37° C., 10% $CO_2$ until they reached about 75% of confluence. The cells were serially passaged for 27 passages, corresponding to about 58 cell generations. The cells were trypsinized and stored in ampoules at $5 \times 10^5$ cells per ml in liquid nitrogen to create a master cell bank (MCB).

One ampoule was removed from the MCB, thawed and transferred into fresh media to create a $28^{th}$ sub-culture, corresponding to about 63 cell generations. The cells were applied to the surface of the vessel at 15,000 cells per square centimeter. The cells were incubated at 37° C., 10% $CO_2$ until they reached about 75% of confluence. The cells were harvested and split into 35 ampoules at $1 \times 10^6$ cells per ml and frozen in liquid nitrogen to create a working cell bank (designated WCB1).

A second ampoule of cells at 27 passages prior to freezing was transferred into fresh media to create a $28^{th}$ sub-culture, corresponding to about 63 cell generations. The cells were applied to the surface of the vessel at 15,000 cells per square centimeter. The cells were incubated at 37° C., 10% $CO_2$ until they reached about 75% of confluence. The cells were harvested and split into 19 ampoules at $5 \times 10^5$ cells per ml which were frozen in liquid nitrogen and stored (designated as MCB+1). One ampoule was then thawed and transferred into fresh media and applied to the surface of the vessel at 15,000 cells per square centimeter for a $29^{th}$ sub-culture corresponding to about 70 cell generations, and incubated at 37° C., 10% $CO_2$ until they reached about 75% of confluence. The cells were harvested and stored in ampoules at $8 \times 10^5$ cells per ml in liquid nitrogen to create a master cell bank 2 (MCB+2).

One ampoule of cells at 29 passages was thawed and transferred into fresh media to create a $30^{th}$ sub-culture, corresponding to about 77 cell generations. The cells were applied to the surface of the vessel at 15,000 cells per square centimeter and were incubated at 37° C., 10% $CO_2$ until they reached about 75% of confluence. The cells were harvested and split into two fractions, one further split into 47 fractions and stored in ampoules at $1.3 \times 10^6$ cells per ml in liquid nitrogen (designated WCBa). The second fraction was further split into 42 ampoules at $1 \times 10^6$ cells per ml and stored in liquid nitrogen (designated WCBb).

Cells sub-cultured from the working cell bank (WCB 1) were thawed and transferred into fresh media. The cells were applied to the surface of the vessel at 15,000 cells per square centimeter and incubated at 37° C., 10% $CO_2$ until they reached about 75% of confluence. The cells were harvested and split into 25 ampoules, each containing 25 million cells in about 1-2 ml and were deposited with the American Type Culture Collection, 10801 University Blvd. Manassas, Va. 20110-2209 U.S.A. These cells are designated as "MMM cells" and were mailed by Federal Express by Howard Green of Harvard Medical School on Oct. 28, 2005 and designated accession number PTA-7190.

Example 2

Preparation of an Immortalized Drug-Resistant Cell Line from 12-13 Day Mouse Embryos Experimental Methods Culture Conditions During Establishment of the MMM Cell Line All cultures were maintained in 100 $mm^2$ tissue culture dishes and were equilibrated with 10% $CO_2$ at 37° C. in a humidified incubator. Calf serum was purchased from HyClone Laboratories Inc. (Logan, Utah). Eagle's medium modified by Dulbecco-Vögt (D-MEM) was purchased from Life Technologies (Gaithersburg, Md.), and all other reagents were analytical grade. Cells were cryopreserved with 10% DMSO in glass ampoules in liquid nitrogen at $1 \times 10^6$ cells per ml.

Transfection of MMM Cells to Produce Double Drug Resistant MMMbz

Plasmid pIB with the ASNBSD gene, encoding blasticidin S deaminase derived from pcDNA6/TR (Invitrogen, Carlsbad, Calif.) (Iuchi, S., et al., 2003, *Proc Natl Acad Sci USA*, 100:2409-14) was digested with EcoRI. Plasmid pVgRXR with the Sh ble gene encoding a zeocin binding protein (Invitrogen, Carlsbad, Calif.) were digested with EcoR V and Not1. These digests containing the intact ASNBSD and Sh ble genes were then introduced into MMM in a buffer (Buffer R) under condition U-30 using the amaxa nucleofector I to produce MMMbz cells.

Use of MMMbz Cells, MEFs and 3T3 to Support hES Cells

MMMbz and 3T3 cells were irradiated at 6000 RADS, and $10^6$ cells were plated in 35 mm dishes in D-MEM supplemented with 10% calf serum on the day before use. MEFs (PMEF-N, Specialty Media), which had already been treated with mitomycin C by the supplier, were similarly plated one day before use in D-MEM supplemented with 10% fetal bovine serum (HyClone Laboratories, Logan, Utah). Human embryonic stem (hES) cells were grown in SR medium equilibrated with 5% $CO_2$. SR medium consists of Knockout D-MEM, supplemented with 20% Knockout Serum Replacement (Knockout SR), 1 mM L-glutamine, 1% MEM non-essential amino acids, 0.1 mM β-mercaptoethanol, and 4 ng/ml bFGF (all components from Life Technologies, Gaithersburg, Md.).

Measurement of Doubling Time

Cultures of MMM cells were photographed in 5 different regions every 24 hours using the Spot digital camera and a Nikon 4× phase contrast objective. Cell numbers were determined from the photographs. Doubling times were estimated by plotting the average cell number per field on a semi-logarithmic ordinate against incubation time.

Detection of Oct4

H9 cultures were fixed in acetone/methanol (1:1) for 15 minutes at 20° C. and stained with monoclonal antibody to Oct4 (SC-5279 diluted 1:100 in phospate-buffered saline (PBS) containing 5% albumin, Santa Cruz Biotechnology, Inc., Santa Cruz, Calif.) overnight at 4° C. The sample was washed with PBS containing 0.1% NP-40 and then incubated with donkey anti-mouse IgG coupled to peroxidase (diluted 1:200 in PBS containing 5% albumin, Jackson ImmunoResearch Laboratories, Inc., West Grove, Pa.) for one hour at room temperature. The sample was again washed and finally incubated with ImmunoPure Metal Enhanced DAB Substrate (Pierce, Rockford, Ill.) for 10 minutes at room temperature. Nuclei containing Oct4 were stained brownish-black. After the substrate was replaced with PBS, the color of the nuclei continued to develop overnight at room temperature. For long-term preservation, PBS was then replaced with glycerol.

Results

The Establishment of the MMM Cell Line

Thirteen embryos from Thieler gestational stage 21 (E12-13) were obtained from mouse strain NMR1. The embryos were removed under aseptic conditions and the head and viscera were discarded. The carcasses were rinsed several times with PBS pH 7.4 and finely minced in 1.0 ml PBS containing 0.3% trypsin. The mince was incubated at 37° C. with additional trypsin solution containing 0.01% EDTA for 10 min, with occasional gentle stirring. The tissue fragments were then allowed to settle and DMEM supplemented with 10% calf serum was added to the supernatant cell suspension. To prepare primary cultures, $10^6$ cells were inoculated into each of ten 100 mm tissue culture dishes. After allowing the cells to attach for 4-5 hours, the medium was changed and incubation was continued.

Figure 1B:
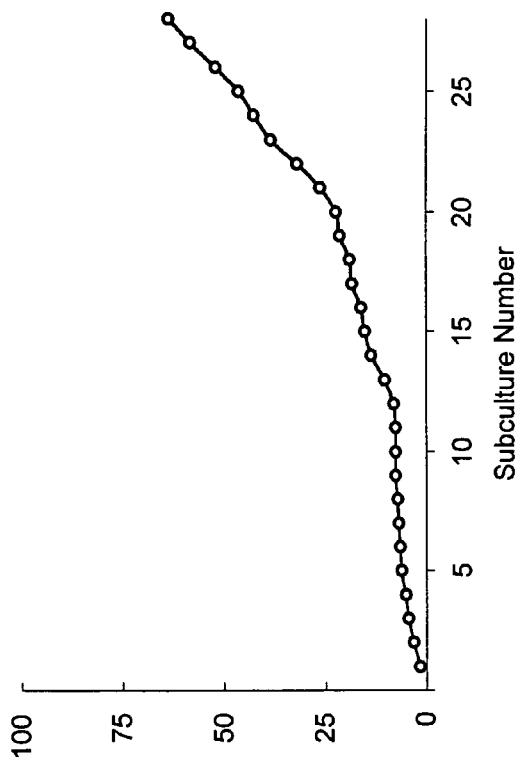

In order to establish the cell line, successive subculture was carried out, taking care to harvest the cells before they reached confluence, as previously described for the establishment of 3T3 cells (Todaro, G. and H. Green, (1963), *J Cell Biol*, 17:299-313). At each subculture, the cells to be harvested from 2-4 dishes were disaggregated with trypsin-EDTA, pooled, and counted; a portion was used to reinoculate at a cell density of $8\times10^5$ per dish and the rest was cryopreserved. Thereafter, the cultures were transferred every 3 days at the same inoculation density as had been used to establish the 3T3 line (15,000/cm$^2$). By subculture number 11, the growth rate of the cells had decreased to a very low value but at subculture 12 the growth rate began to increase, indicating the beginning of the development of an immortalized cell line (FIG. 1A). The growth rate continued to increase until transfer 22, when it attained an average rate of about 5 cell doublings per subculture (1.1 cell doublings per day). At subculture 28, the population had undergone about 63 cell doublings (FIG. 1B). A large number of cultures was cryopreserved at transfer 27 in order to prepare a master cell bank, as previously described in Example 1.

The Adhesiveness of MMM Cells

The MMM line showed an uncommon ability to adhere to and spread over the surface of the culture vessel. Lethally irradiated MMM cells, when inoculated at a density of $3\times10^4$ cells/cm$^2$ adhered to form a quarter-confluent monolayer by the next day. Over the following two days, the MMM cells spread to cover the entire surface. For supporting the growth and pluripotentiality of H9 cells the MMM cells are inoculated at a four-fold higher density ($1.2\times10^5$/cm$^2$). This ensured that the H9 cells will be unable to make contact with the vessel surface. The 3T3 cells did not have the same adhesiveness and ability to spread as the MMM cells.

Production of Drug-Resistant MMM Cells

Figure 2A:
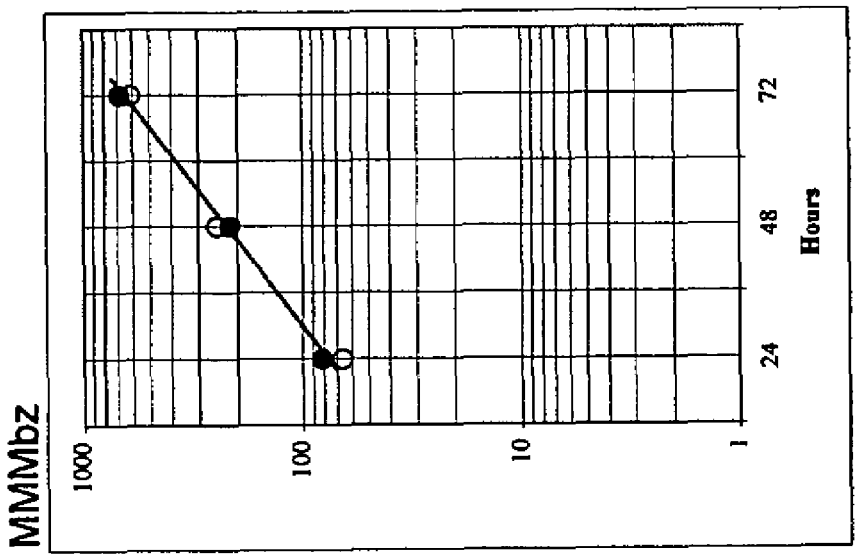
FIG. 2. Killing of MMM cells by blasticidin and zeocin and the production of a subline resistant to both drugs. A) Graph showing growth of the MMM cells in the presence or absence of antibiotic. ● Represents growth of MMM cells in the absence of antibiotic (Td=16 hours), ■ represents effect of adding blasticidin to 5 μg/ml at time of inoculation, ▲ represents effect of adding zeocin to 400 μg/ml at time of inoculation and ○ represents effect of adding both antibiotics at the time of inoculation. B) Growth rate of MMM cells made resistant to blasticidin and zeocin (MMMbz) by nucleofection with the genes for resistance to both drugs. ● represents no drug addition, ○ represents both drugs added. Td in presence of both drugs=16 hours.

MMM cells inoculated from a 3 day growing culture grew exponentially in D-MEM with a doubling time of 16 hours (FIG. 2A). When blasticidin was added to 5 µg/ml at the time of inoculation, the cell number decreased by the following day, and by 48 hours the number of attached cells was less than 0.1% that of the untreated MMM cells. When, to a similar culture, zeocin was added to 400 µg/ml, growth was immediately arrested and the cells became flattened but did not detach from the dish.

In order to make MMM cells resistant to these antibiotics, MMM cells were nucleofected with the blasticidin resistance gene (encoding blasticidin S deaminase). After cultivation of the cells for 2 days without antibiotic, blasticidin was added to 5 µg/ml. This killed most cells, but numerous colonies of resistant cells appeared in the following days. The culture was transferred twice with dilution in the presence of blasticidin to completely remove any sensitive cells.

Figure 2B:
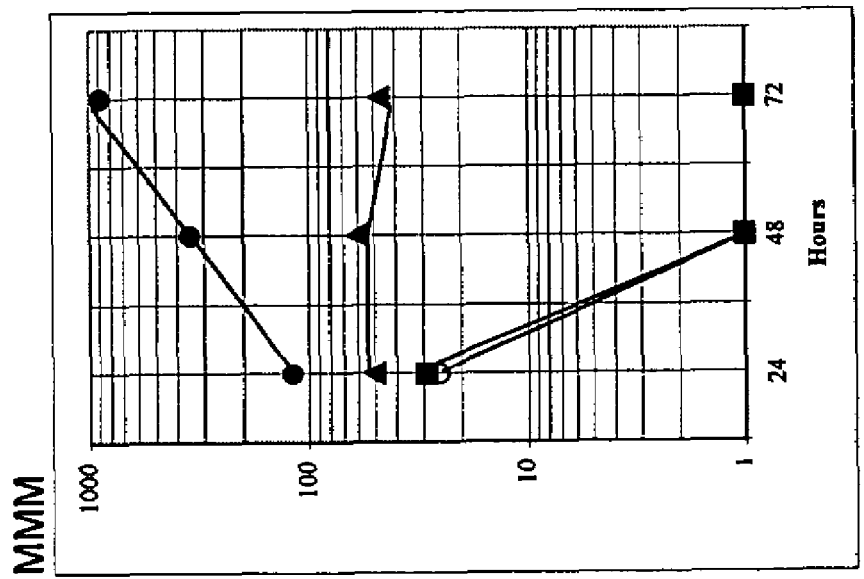

The resulting blasticidin-resistant culture was then nucleofected with the zeocin resistance gene (encoding the zeocin-binding protein), and selection was carried out by adding zeocin to 400 µg/ml, in addition to the blasticidin. Flattened cells pseudo-resistant to zeocin were eliminated by transfer with dilution over the following 10 days. The surviving cells (MMMbz), like the wild type cells, grew in D-MEM with a doubling time of 16 hours (FIG. 2B), and their growth rate was unaffected by the presence of both antibiotics.

Growth of Human ES Cells (H9) Supported by MEFs, MMMbz and 3T3

Cells of each supporting type were treated by irradiation or with mitomycin C and $10^6$ cells were plated in 35 mm dishes. Growing cultures of H9 cells were trypsinized and $1.1\times10^4$ dissociated single cells were inoculated into each dish and fed with SR medium for 5 days.

By the day after inoculation, small colonies appeared on all supporting cell types. Later, differences in morphology between colonies on different supporting cells became evident. This is shown by phase microscopy of the colonies on day five (FIG. 3). The colonies on MMM cells were more angular and had more sharply defined margins than colonies on MEFs. The colonies on MEFs frequently had dome-like structures projecting into the medium. In contrast on 3T3 cells, H9 colonies had no clearly defined margin.

Oct4 Expression by Cells of H9 Colonies on Different Supporting Cell Types

Oct4 is one of a number of transcription factors of the POU family (Scholer, H. R., 1991, *Trends Genet*, 7(10):323-9). It was first discovered in early embryos, ES cells and primordial germ cells (Scholer, H. R., et al., 1989, *EMBO Journal*, 8(9): 2551-7; Scholer, H. R., et al., 1989, *EMBO Journal*, 8(9): 2543-50), and is specific to the lineage perpetuating the germ-line (Scholer, H. R., et al., 1990, *EMBO Journal*, 9(7):2185-95). By day 8.5, Oct4 is lost from all cells of the mouse embryo except the primordial germ cells (Scholer, H. R., et al., 1990, *EMBO Journal*, 9(7):2185-95). Oct4 has been used extensively as the most reliable marker of cultured ES cells, since it is a determinant of full pluripotentiality (Nichols, J., et al., 1998, *Cell*, 95(3):379-91; Niwa, H., et al., 2000, *Nat Genet*, 24(4):372-6; Schuldiner, M., et al., 2000, *Proc Natl Acad Sci USA*, 97(21):11307-12; Pesce, M. and H. R. Scholer, 2001, *Stem Cells*, 19(4):271-8; Green, H., et al., 2003, *Proc Natl Acad Sci U S A*, 100(26):15625-30; Velkey, J. M. and K. S. O'Shea, 2003, *Genesis*, 37(1):18-24; Matin, M. M., et al., 2004, *Stem Cells*, 22(5):659-68).

Figure 4:
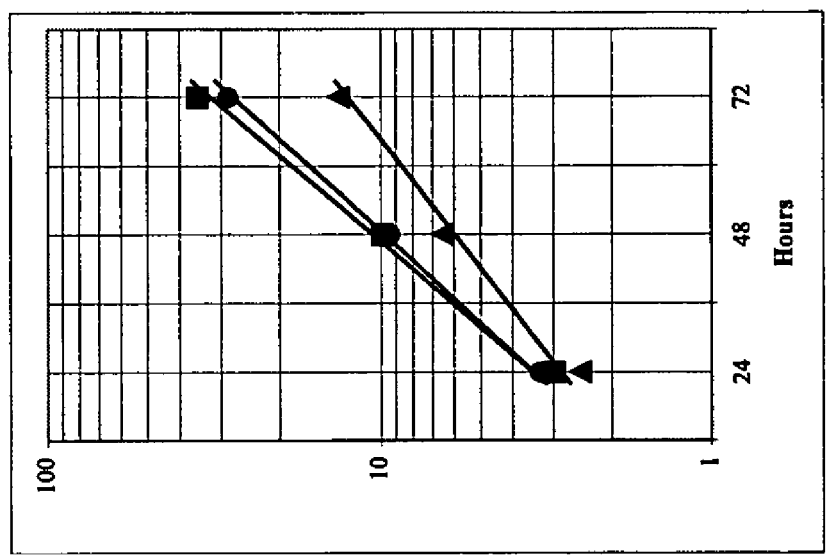
FIG. 4. Graph showing short-term growth (3 days) of Oct4-containing H9 cells on each supporting cell type. At three intervals after inoculation, the number of Oct4-positive cells was counted in each of 20 colonies of H9 cells and the mean number calculated. ● represents growth on MEFs (Td=15 hrs.), ■ represents growth on MMMbz (Td=14 hrs.), ▲ represents growth on 3T3 (Td=19 hrs.).

To analyze the differences between the H9 cells cultured on different supporting cells, the cultures were stained for Oct4 with a specific antibody conjugated to horseradish peroxidase, using a metal enhanced substrate kit to develop a color seen under visible light. The nuclear staining of the H9 cells was sufficiently clear to permit counting the number of Oct4-containing H9 cells during the first three days. The doubling times were 14 to 15 hours on both MMMbz and MEFs and 19 hours on 3T3 (FIG. 4).

Figure 5:
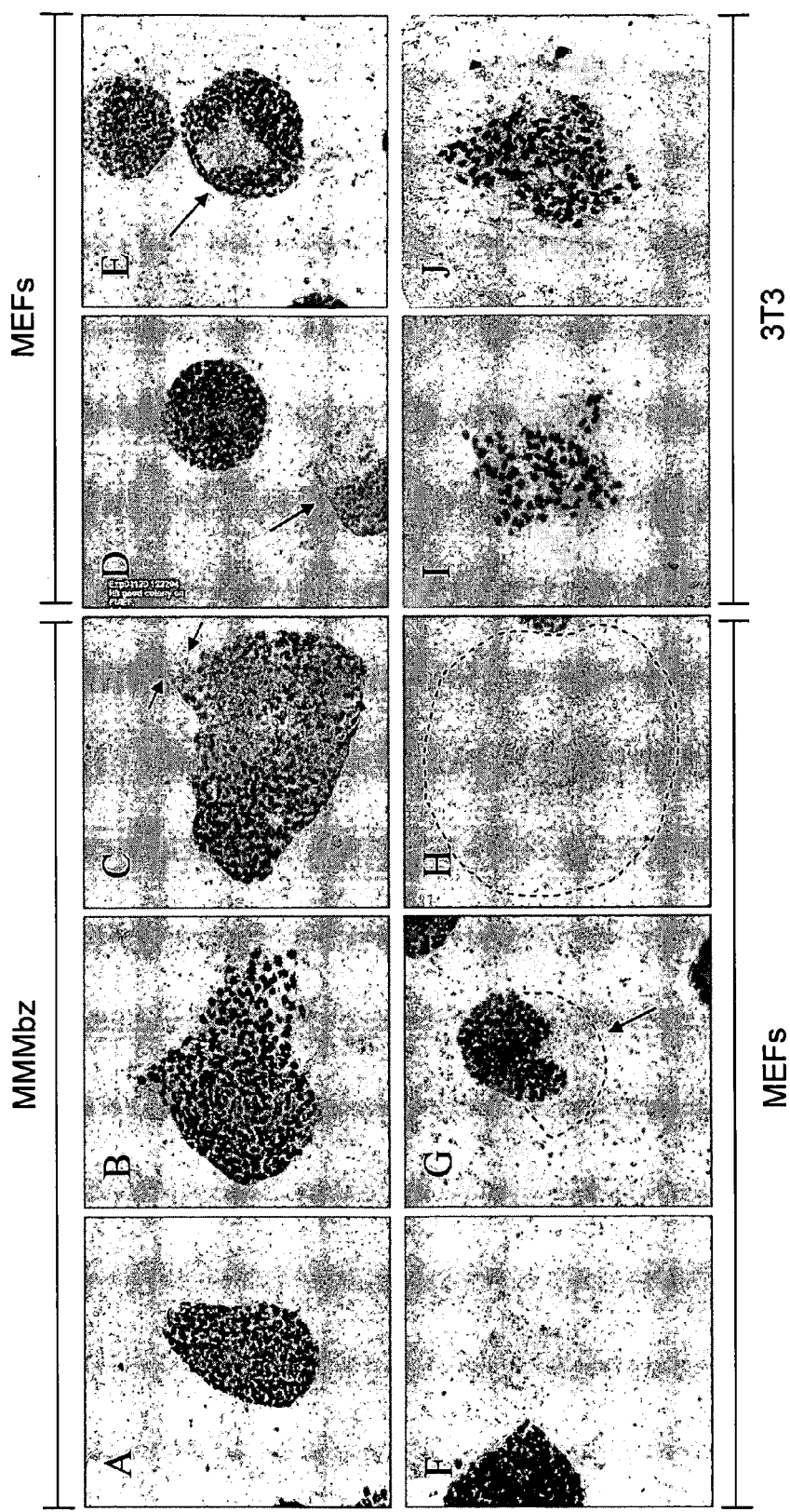
FIG. 5. Digitized photomicrographic image of 5 day colonies of H9 stained for Oct4. A-C) Represents H9 cells grown on MMM cells. Arrows indicate cells that may be losing Oct4. D-H) Represents H9 cells grown on MEFs cells. Arrows indicate possible mosaics with regions containing or lacking Oct4. I-J) Represents H9 cells grown on 3T3 cells.

At five days, H9 colonies on MMMbz cells remained homogeneous with respect to Oct4 expression (FIG. 5). In contrast, the colonies on MEFs were variable. In some of these MEF colonies, all cells possessed Oct4, while in others all cells lacked Oct4. Still other colonies were mosaics containing regions possessing and lacking Oct4. These regions could be located one within the other or one adjacent to the other and the regions lacking Oct4 appeared related to dome-like structures visible under phase microscopy (FIG. 3). A comparison of the number of colonies containing Oct4 with the number of colonies lacking Oct4, either completely or partially (mosaic), is shown in Table 1. The ratio between the two was 0.93 for MEFs and 56 for MMMbz.

The ability of 3T3 cells to support the growth of H9 cells was clearly inferior to that of both MEFs and MMM. The number of Oct4+cells in the colonies was much lower and the cells were dispersed, rather than compact. The number of cells undergoing differentiation appeared to be much greater. The 3T3 cells are thus not as suitable apparently for maintaining the proliferation of H9 cells in a pluripotential state.

Drug Selection of Transfected H9 Cells on Drug-Resistant MMM Cells

Figure 6:
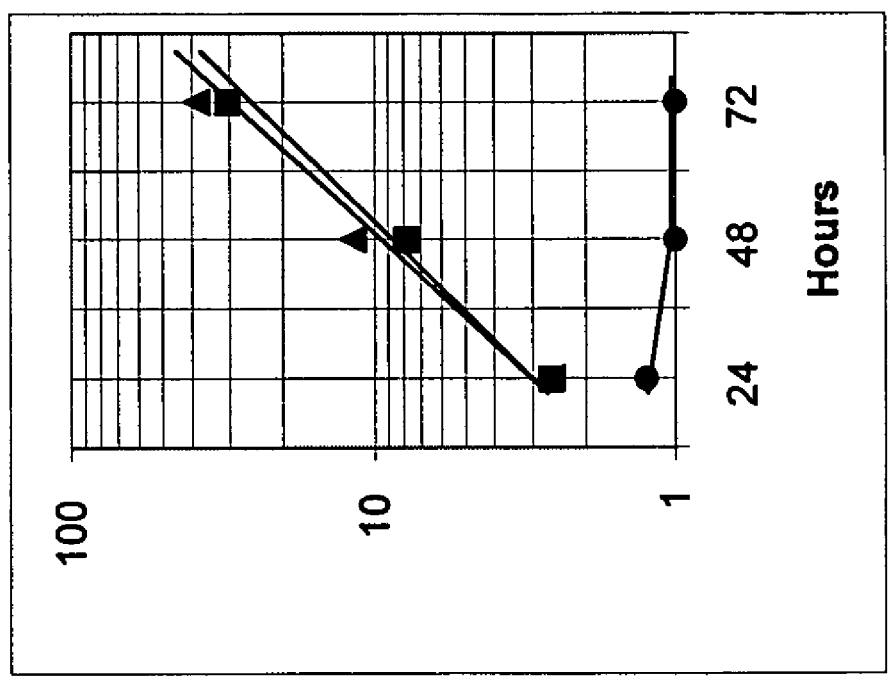
FIG. 6. Graph showing growth of zeocin-resistant H9 cells transfected with the gene encoding the zeocin binding gene, supported by irradiated MMMbz cells. Growth of the H9 cells was followed by counting the number of cells in each of 20 colonies and calculating the mean. ▲ and ■ represent two independent experiments. ● Represent control untransfected cells.

MEFs are not resistant to the drugs zeocin and blasticidin and therefore cannot be used to support the growth of hES cells selected with those drugs. MMMbz cells were used to support the growth of H9 cells transfected with plasmid pVgRXR containing the zeocin-binding gene (Sh blue). For the transfection, 1 µg of the plasmid was added to 0.6-0.75× $10^6$ H9 cells suspended in Buffer V and introduced using nucleofector I, condition T16, as defined by commercially available protocols such as those by amaxa, Inc. The cultures were propagated for three days without antibiotics and then trypsinized for selection in the presence of zeocin at 100 µg/ml. Most cells died on the following day, but a few colonies appeared after two days. From separate cultures, two independent colonies were isolated and while supported by MMMbz, their growth was examined in the presence of zeocin at 25 µg/ml. The average cell number per colony increased with Td of 14 to 15 hours (FIG. 6). Control H9 cells were unable to grow.

Discussion

Nature of a Cell Line Derived from Early Embryos

Most work on the cultivation of ES cells has been carried out using short term cultures of supporting mesenchymal cell types. The advantages of substituting an immortalized cell line in place of a short term cell line include: reproducibility, ease of preparing large amounts, and reduction of expense.

The 3T3 line was evolved from 17-19 day mouse embryos (Todaro, G. and H. Green, 1963, *J Cell Biol*, 17:299-313). Sublines (3T3-J2) have been used extensively for the propagation of human keratinocytes on a large scale (Rheinwald, J. G. and H. Green, 1975, *Cell*, 6(3):331-43; Green, H., et al., 1979, *Proc Natl Acad Sci U S A*, 76(11):5665-8; the entire contents of each of which are herein incorporated by reference). 3T3 cells support the growth of hES cells but do not permit the colonies to retain the desired compactness or an adequate number of cells containing Oct4. The migration and dispersion of the hES cells further supports the conclusion that 3T3 cells are not optimal for the propagation of hES cells. It is suggested that the superiority of MMM cells for this purpose is due to their relatively greater ability to spread on the vessel surface, their stronger adhesiveness to that surface, and their greater capacity to prevent the hES cells from making contact with that surface.

MMM cells were developed using a transfer regimen not very different from the one used for the development of 3T3 cells. The embryos from which MMM was derived were much younger (12-13 days).

Preserving Oct4

Many studies have supported the concept that loss of Oct4 from ES cells is reliably associated with loss of pluripotentiality. The greater loss of Oct4 from H9 cells cultured with MEFs than from those cultured with MMM is likely related to the observation that ES cells in piled up colonies tend to lose Oct4 (Thomson, J. A., et al., 1998, [erratum appears in Science Dec. 4, 1998 ;282(5395):1827.]*Science*, 282(5391):1145-7; the entire contents of which are herein incorporated by reference). The five day H9 colonies shown under phase microscopy in FIG. 3 are usually more flattened when growing on MMM than on MEFs and lack the domes corresponding to regions of loss of Oct4 in the mosaic colonies formed on MEF's (FIG. 5). It is suggested that this is the reason that MMM cells produce better maintenance of Oct4 of the H9 line than do MEFs.

Use of Drug-Resistant MMM Cells For Introduction of Genes into hES Cells

It has been shown above that zeocin-resistant MMM cells can be used to select H9 cells into which the gene for zeocin-resistance has been introduced by transfection. A gene capable of modifying behavior of the hES cells can be introduced together with the gene for drug resistance. If the two are linked, the selected cells should possess the modifying gene.

TABLE 1

Effect of supporting cell type on frequency of H9 colonies lacking Oct4 partially or completely.

| | Number of Colonies | | |
|---|---|---|---|
| Cell Type | (I) Oct4$^+$ | (II) Oct4$^-$ + Oct4$^{mosaic}$ | (I)/(II) |
| MEFs | 118 | 127 | 0.93 |
| MMMbz | 169 | 3 | 56 |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

We claim:

1. A composition comprising MMM cells, or progeny thereof, deposited with the ATCC under accession number PTA-7190.

* * * * *

UNITED STATES PATENT AND TRADEMARK OFFICE
CERTIFICATE OF CORRECTION

| | |
|---|---|
| PATENT NO. | : 7,413,900 B2 |
| APPLICATION NO. | : 11/263549 |
| DATED | : August 19, 2008 |
| INVENTOR(S) | : Howard Green et al. |

It is certified that error appears in the above-identified patent and that said Letters Patent is hereby corrected as shown below:

Title Page, Item (73)

At item 73 (Assignee): Please add Centro de Investigacion y de Estudios Avanzad os del I.P.N., D.F., Mexico.

Signed and Sealed this
Twenty-eighth Day of December, 2010

David J. Kappos
*Director of the United States Patent and Trademark Office*